(12) United States Patent
Bott et al.

(10) Patent No.: US 6,946,280 B1
(45) Date of Patent: Sep. 20, 2005

(54) ENZYME MULTIMER AND PROCESS OF PRODUCING SAME

(75) Inventors: Richard L. Bott, Burlingame, CA (US); Christian Paech, Daly City, CA (US); Shan Wu, Castro Valley, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 08/625,487

(22) Filed: Mar. 29, 1996

(51) Int. Cl.[7] ............................. C12N 9/56; C12N 9/50; C12N 9/96
(52) U.S. Cl. ...................... 435/222; 435/219; 435/188
(58) Field of Search ................................ 435/219, 188, 435/187, 195, 222, 189

(56) References Cited

U.S. PATENT DOCUMENTS

| | | | | |
|---|---|---|---|---|
| 4,844,897 A | * | 7/1989 | Maeda et al. ............... | 424/94.3 |
| 4,853,871 A | * | 8/1989 | Pantoliano et al. ........... | 701/99 |
| 4,908,773 A | * | 3/1990 | Pantoliano et al. .......... | 702/138 |
| 5,061,788 A | * | 10/1991 | Certa .......................... | 530/350 |
| 5,185,258 A | * | 2/1993 | Caldwell et al. ............ | 435/220 |
| 5,500,364 A | * | 3/1996 | Christianson et al. ....... | 435/221 |
| 5,795,761 A | * | 8/1998 | Powers et al. ............... | 435/190 |

FOREIGN PATENT DOCUMENTS

| | | | | |
|---|---|---|---|---|
| EP | 155832 A2 | * | 9/1985 | ........... C12P/21/00 |
| JP | 06207941 A | * | 7/1994 | ......... G01N/33/576 |
| WO | WO 9410191 A1 | * | 5/1994 | ............ C07K/3/06 |
| WO | WO 9737007 A1 | * | 10/1997 | ............ C12N/9/96 |

OTHER PUBLICATIONS

Takeda et al., "On the Specific Association of Porcine Erythrocyte Catalase Caused by Formation of Disulfide Cross–Links" (1977) Biochim. Biophys. Acta, 481 (2), 420–430.*
Cappel et al., "Oxidative Inactivation of 3–Hydroxy–3–methylglutaryl–coenzyme A Reductase and Subunit Cross–Linking Involve Different Dithiol/Disulfide Centers" (1993) J. Biol. Chem., 268(1), 342–348.*
Gutte et al., "Design, Synthesis and Characterization of a 34–Residue Polypeptide that Interacts with Nucleic Acids" (1979) Nature, 281, 650–655.*
Peters et al., "Chemical Cross–Linking Reagents and Problems in Studies of Membrane Structure" (1977) Ann. Rev. Biochem., 46, 523–551.*
Brennan et al., "Preparation of bispecific Antibodies by Chemical Recombination of Monoclonal Immunoglobulin G[1] Fragments," *Science* (1985) 229:81–83.
Bulow et al., "Multienzyme Systems Obtained by Gene Fusion," *Tibtech* (1991) 9:226–231.
Bulow, "Artificial Bifunctional Enzyme: A tool To Improve Consecutive Enzymes Reactions and Cell Metabolism," *American Chemical Society* (1993) 14:174–184.

Bulow, "Characterization of an Artificial Bifunctional Enzyme, β–Galactosidase/galactokinase, Prepared by Gene Fusion," *FEBS* (1987) 163:443–448.
Byrne et al., "Chemically Crosslinked Protein Dimers: Stability and Dematuration effects," *Protein Science* (1995) 4:2545–2558.
Chen et al., "Production of Multimeric Forms of CD4 through a Sugar–based Cross–linking Strategy," *The Journal of Biological Chemistry* (1991) 266/27:18237–18243.
DeSilva et al., "Solid Phase Synthesis of Bifunctional Antibodies," *Journal of Immunological Methods* (1995) 188:9–19.
Friedrich, "Supramolecular Enzyme Organization: Quaternary Structure and Beyond." *Pergamon Press, Oxford* (1984) 2–3.
Glennie et al., "Preparation and Performance of Bispecific f(ab'γ)$_2$ Antibody Containing Thioether–linked Fab'γ Fragments[1]," *The Journal of Immunology* (1987) 139/7:2367–2375.
Ljungcrantz et al., "Construction and Characterization of a Recombinant Tripartite Enzyme, Galactose Dehydrogenase/β–Galactosidase/Galactokinase," *FEBS* (1990) 275/1.2:91–94.
Ljungcrantz et al., "Construction of an Artificial Bifunctional Enzyme, β–Galactosidase/Galactose Dehydrogenase, Exhibiting Efficient Galactose Channeling," *Biochemistry* (1989) 28:8786–8792.
Pepinsky et al., "The Increased Potency of Cross–linked Lymphocyte Function–associated Antigen–3 (LFA–3) Multimers is a Direct Consequence of Changes in Valency," *The Journal of Biological Chemistry* (1991) 266/27:18244–18249.
Reznik et al., "Streptavidins with Intersubunit Crosslinks have Enhanced Stability," *Nature Biotechnology* (1996) 14:1007–1011.
Siegbahn et al., "Preparation and Partial Characterization of a Soluble Site–to–Site Directed Enzyme Complex Composed of Alcohol Dehydrogenase and Lactate Dehydrogenase." *Applied Biochem. and Biotech.* (1986) 12:91–105.
Srere et al., "An Immobilized Three–Enzyme System: A model for Microenvironmental Compartmentation in Mitochondria." *Proc. Nat. Acad. Sci.* (1973) 70/9:2534–2538.
Yi et al., "Structural and Functional Studies of Cross–linked G$_O$ Protein Subunits," *The Journal of Biological Chemistry* (1991) 266/6:3900–3906.

* cited by examiner

*Primary Examiner*—Jean C. Witz
*Assistant Examiner*—Susan Hanley
(74) *Attorney, Agent, or Firm*—Genencor International, Inc.

(57) ABSTRACT

An enzyme multimer is provided which comprises a plurality of monomer units including a first monomer unit having enzymatic activity and a second monomer unit having enzymatic activity, wherein each of the first monomer unit and the second monomer unit comprise a cysteine residue and the cysteine residues of each monomer unit are covalently bound to each other through a disulfide bond to covalently attach the first monomer unit to the second monomer unit.

2 Claims, 5 Drawing Sheets

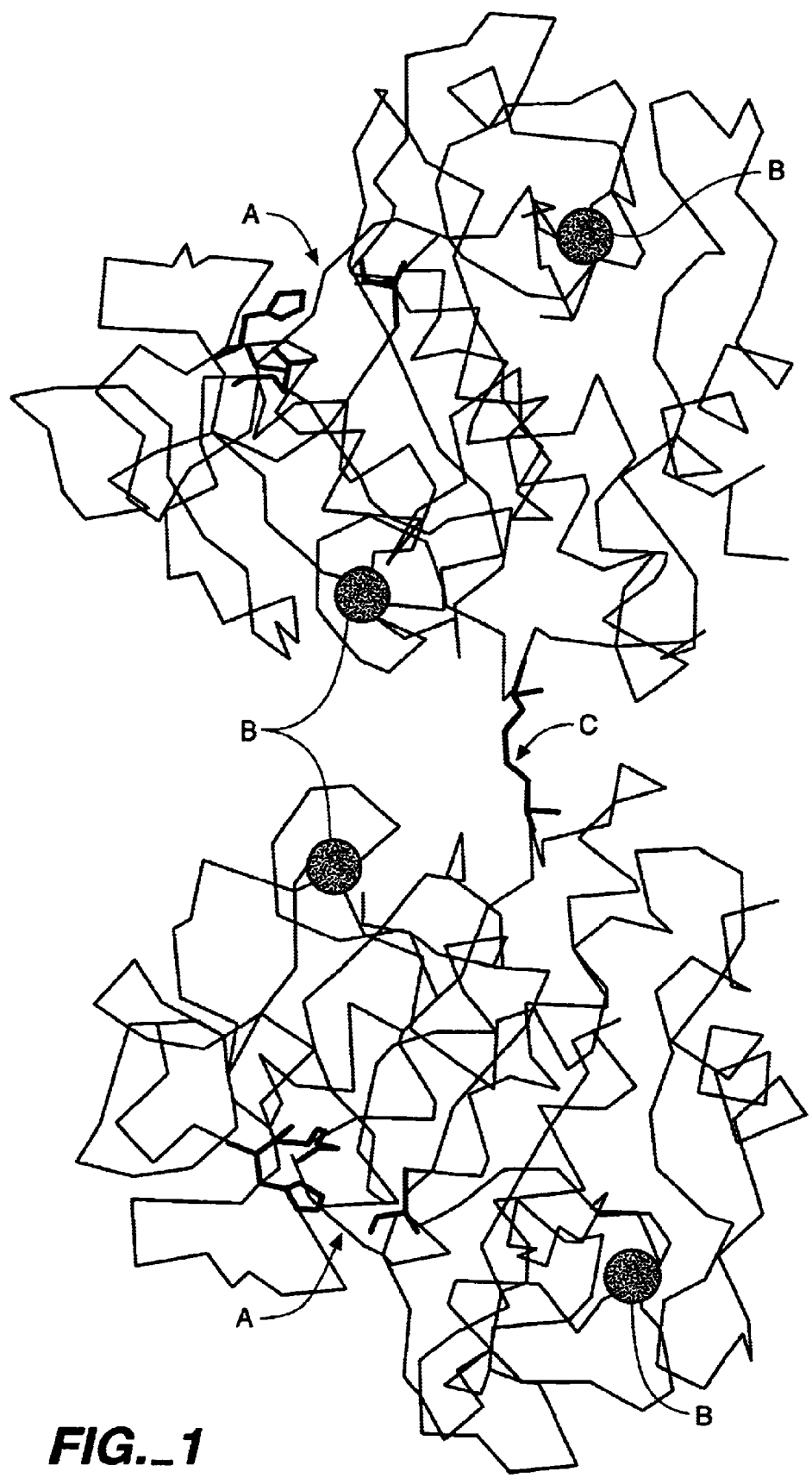
FIG._1

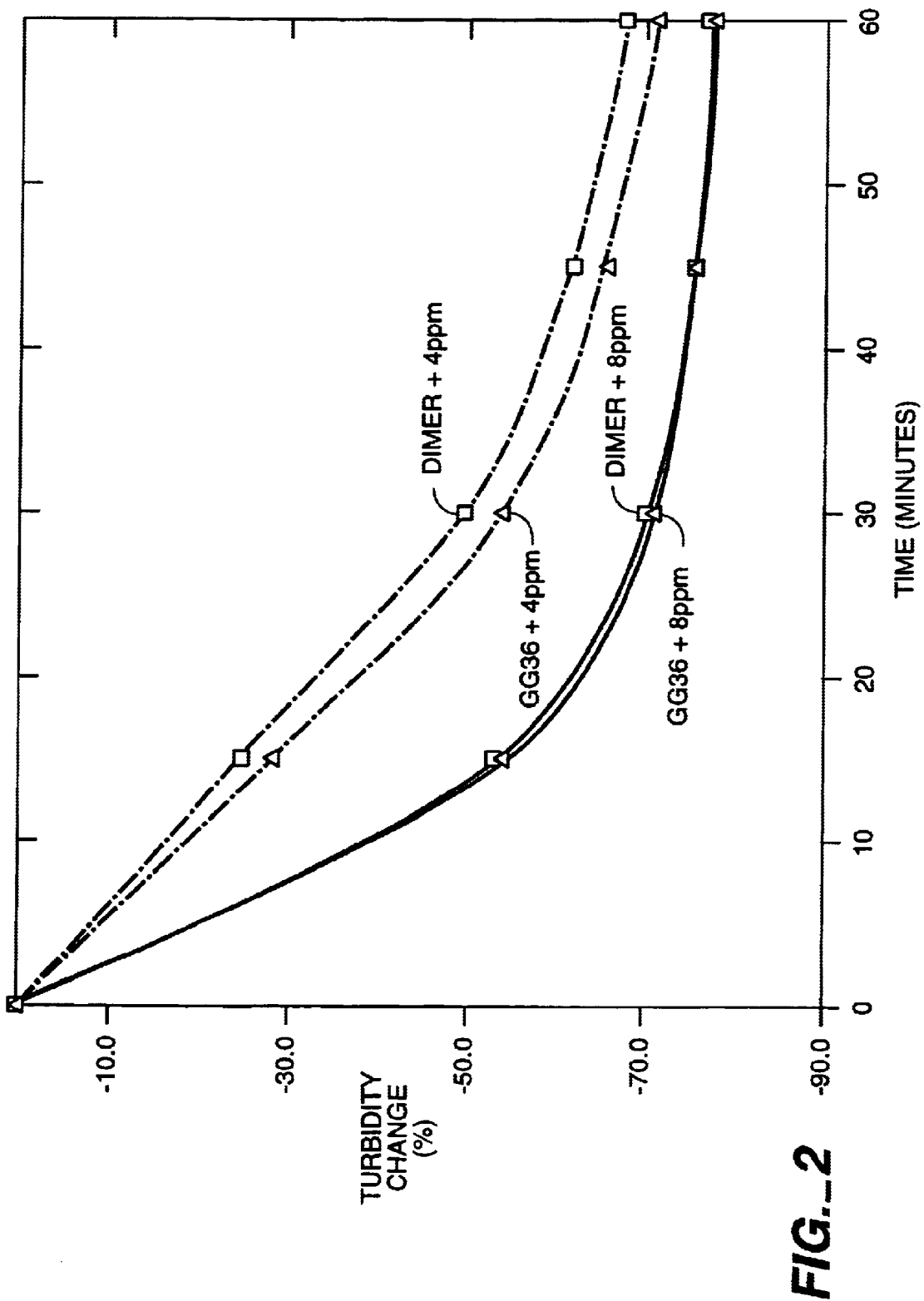
FIG._2

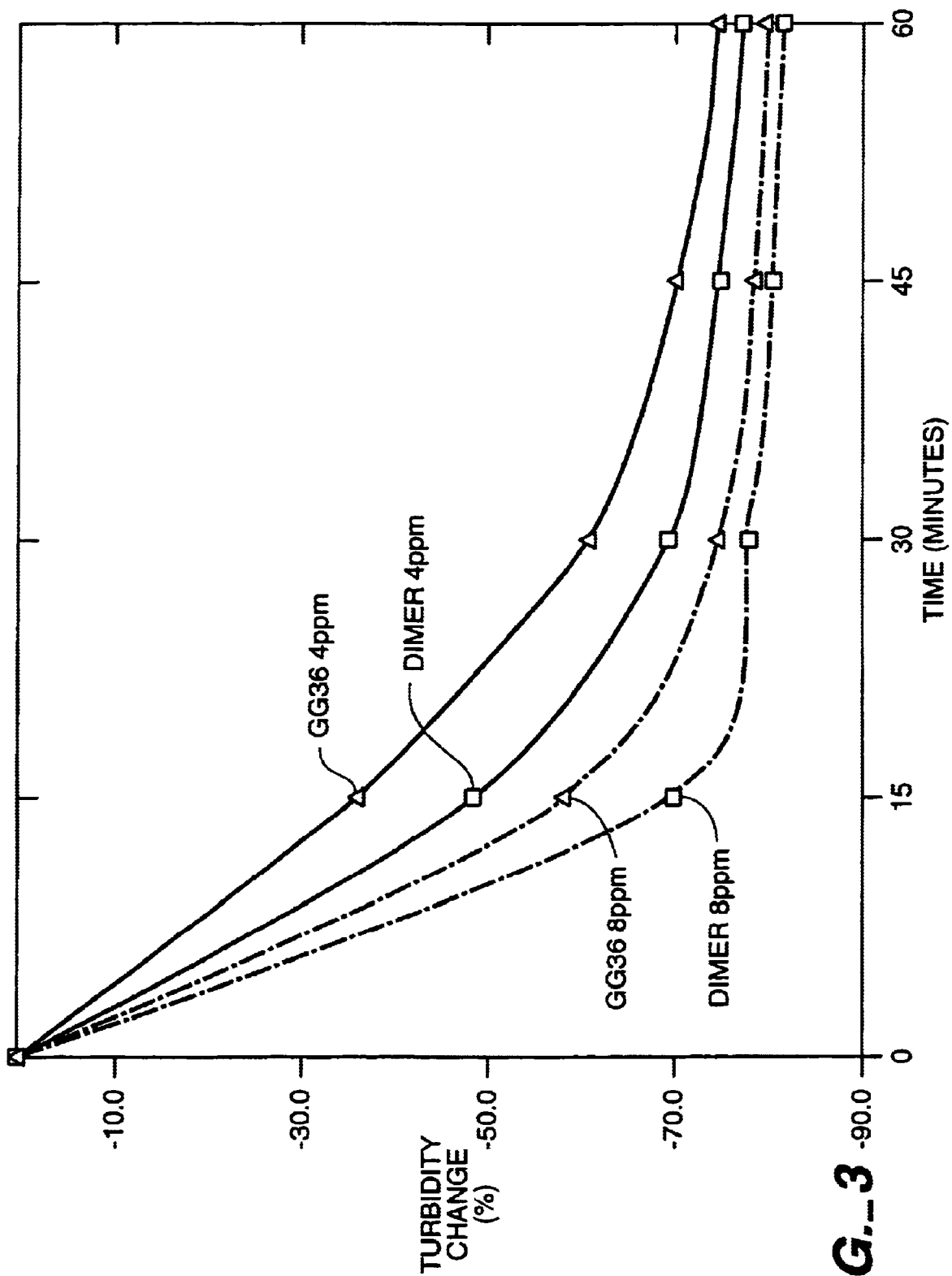
FIG._3

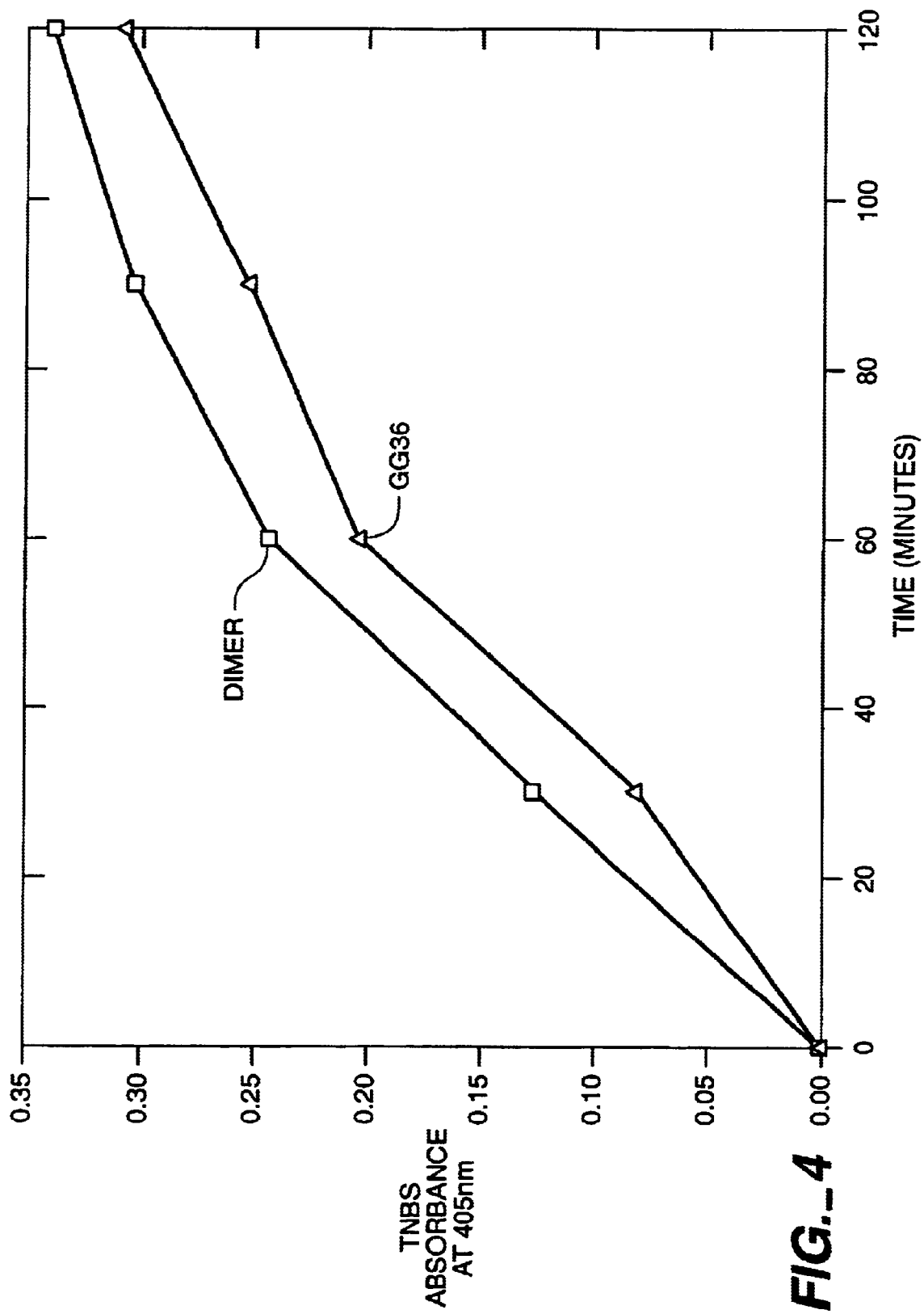
FIG._4

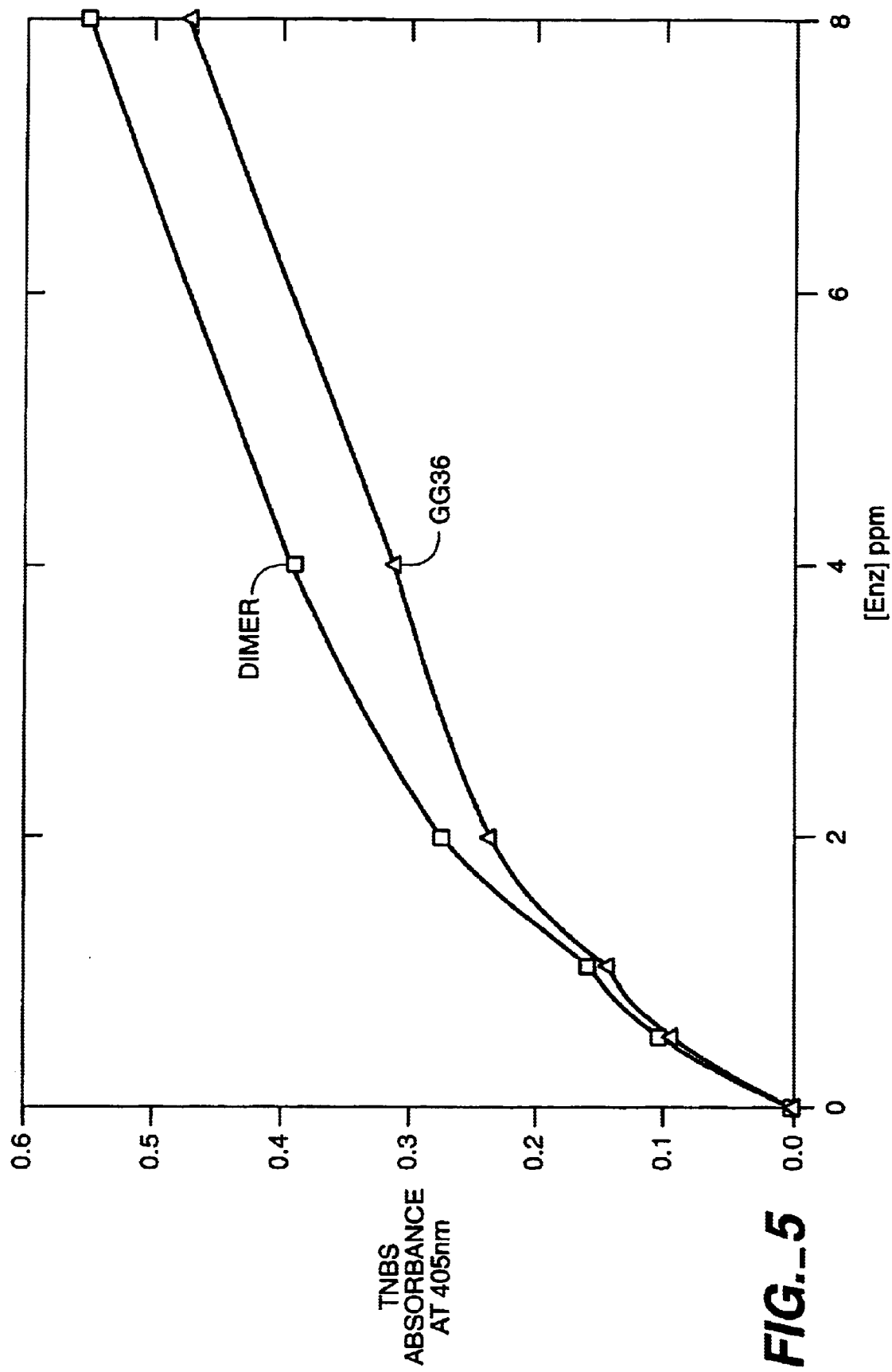
FIG._5

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 1
cgtggattga ccggttgtgg tgtaaaagtt                    30

US 6,946,280 B1

ENZYME MULTIMER AND PROCESS OF PRODUCING SAME

The U.S. Government has a paid-up license in this invention and the right in limited circumstances to require the patent owner to license others on reasonable terms as provided for by the terms of Cooperative Research Agreement 70NANB5H1138 awarded under the ATP-NIST program.

BACKGROUND OF THE INVENTION

1. Field of the Invention

The present invention is related to the production of an enzyme aggregate having Improved performance and use characteristics. More particularly, the present invention is related to an enzymatic multimer which comprises monomer units of either homologous or heterologous origin which have been covalently bonded to each other. The enzymatic multimer of the invention has advantages such as improved performance in terms of activity, allergenicity or enzyme-substrate interactions.

2. State of the Art

Multiple enzyme aggregates have been suggested for decreasing the allergenicity of the component enzyme(s) by increasing their size. For example, PCT Publication No. 94/10191 discloses oligomeric proteins which display lower allergenicity than the monomeric parent protein and proposes several general techniques for increasing the size of the parent enzyme. Additionally, enzyme aggregates have shown improved characteristics under isolated circumstances. For example, Naka et al., Chem. Lett., vol. 8, pp. 1303–1306 (1991) discloses a horseradish peroxidase aggregate prepared by forming a block copolymer via a 2-stage block copolymerization between 2-butyl-2-oxazoline and 2-methyl-2-oxazoline. The aggregate had over 200 times more activity in water saturated chloroform than did the native enzyme.

Cross-linked enzymes prepared by the addition of glutaraldehyde has been suggested as a means of stabilizing enzymes. However, cross-linking often leads to losses in activity compared to native enzyme. For example, Khare et al., Biotechnol. Bioeng., vol. 35, no. 1, pp. 94–98 (1990) disclose an aggregate of $E.\ coli$ β-galactosidase produced with glutaraldehyde. The enzyme aggregate, while showing improvement in thermal stability at 55° C., had an activity of only 70.8% of that of the native enzyme which was, however, considered a good retention of activity after cross-linking.

As is understood from above, several alternatives have been developed by those of skill in the art seeking to produce aggregated enzymes for the purpose of decreasing allergenicity or altering activity parameters. However, a problem common to each of these processes is that, when preparing aggregated enzymes according to these prior art teachings, it is not believed feasible to predict how certain enzymes will behave in the aggregated form. Moreover, the formation of an enzyme aggregate according to these prior art teachings is an inexact science which is highly dependent on fortuity, thus presenting a significant barrier to the preparation of a multienzyme aggregate having pre-selected activities.

To overcome these problems, researchers have developed enzymatic aggregates which comprise predetermined fusion proteins. In a typical fusion protein, the gene for one protein is fused to the gene for a second protein and the resultant combination enzyme is expressed as an integral unit. Such fusion proteins, as applied to enzymes, while providing an important advantage in terms of providing a single protein combining multiple enzymatic activities, are problematic in terms of expression and/or secretion in a suitable host cell. For example, proteolytic cleavage, improper folding and secretion problems within the cell resulting from or due to size or tertiary structure represent significant drawbacks of fusion enzyme technology.

Accordingly, it would be desirable to develop a new means of preparing multiple enzyme systems useful for medical, diagnostic or industrial purposes which is capable of being customized in terms of included enzymatic activities and positional interrelationships of those enzymes so as to maximize the kinetics of the specific application. It would further be desirable to develop a new means of preparing multiple enzyme systems which do not have problems in expression and secretion characteristic of fusion proteins, and which allow flexibility in determining the conformation of the resulting multiple enzyme. However, the prior art fails to provide a means for producing a multiple enzyme system having such characteristics.

SUMMARY OF THE INVENTION

It is an object of the present invention to provide an enzyme multimer which has altered activity, an altered activity profile, altered environmental requirements or other altered performance characteristics.

It is an object of the present invention to provide an enzyme multimer which may be easily produced and incorporated into existing processes and products.

It is an object of the present invention to provide an enzyme multimer which may possess a plurality of enzymatic activities.

It Is an object of the present invention to provide an enzymatic activity which may have improved allergenicity characteristics.

According to the present invention, an enzyme multimer is provided comprising a plurality of monomer units including a first monomer unit having enzymatic activity and a second monomer unit having enzymatic activity, wherein each of said first monomer unit and said second monomer unit comprise a cysteine residue and said cysteine residues are covalently bound to each other through a thio-mediated bond to covalently attach said first monomer unit to said second monomer unit.

BRIEF DESCRIPTION OF THE DRAWINGS

FIG. 1 illustrates a model of the tertiary structure of a dimer deduced from the actual crystal structure measurements of GG36 monomer units. The active site of the monomer units is designated as region "A", the calcium ions are designated as region "B" and the position of the introduced cysteine and thio-mediated covalent bond designated as region "C".

FIG. 2 illustrates the comparative results of skim milk protein hydrolysis activity of the S24C (monomer) and GG36 (monomer) at 4 ppm and 8 ppm in the presence of DTT.

FIG. 3 illustrates the comparative results of skim milk protein hydrolysis activity of the GG36-S24C dimer and GG36 (monomer) at 4 ppm and 8 ppm.

FIG. 4 illustrates the time course of keratin hydrolysis by S24C (dimer) and GG36 (monomer) at 8 ppm over 120 minutes.

FIG. 5 illustrates the activity of S24C (dimer) and GG36 (monomer) on keratin at from 0–8 ppm after 120 minutes.

DETAILED DESCRIPTION OF THE INVENTION

According to the invention, an enzyme multimer is provided which comprises a plurality of monomer units including a first monomer unit having enzymatic activity and a second monomer unit having enzymatic activity, wherein each of the first monomer unit and the second monomer unit comprise a cysteine residue and the cysteine residues of each monomer unit are covalently bound to each other through a disulfide bond to covalently attach the first monomer unit to the second monomer unit. Surprisingly, Applicants have discovered that the enzyme multimer according to the invention displays increased activity.

"Enzyme multimer" means a single protein molecule composed of at least two individual enzymes which are covalently bound together. Thus, an enzyme multimer according to the present invention will have at least two distinct sites capable of catalyzing a chemical reaction, i.e., at least two active sites. The individual enzymes, referred to as "monomer units" herein, may comprise any protein or peptide which possesses enzymatic activity and is not limited to known or existing enzymes. A suitable monomer unit comprises a hydrolase such as a protease, a cellulase, an amylase, an esterase, a lipase or a hemicellulase; an enzyme which catalyzes an oxidation-reduction reaction (an oxidoreductase) such as a peroxidase, a microperoxidase, a laccase, a ligninase, an oxidase, a NADH reductase, a 2,5 DKG reductase; a transferase; an isomerase such as a glucose isomerase or a xylose isomerase; a lyase; or a ligase or synthetase. It is contemplated that the monomer units of the multimeric enzyme may be the same enzyme, the same activity from a different enzyme protein, or entirely different enzymes. Thus, the monomer units may be "homologous" or "heterologous." In a preferred embodiment, the monomer units comprise a bacterial protease or amylase, more preferably a bacterial protease or amylase derived from *Bacillus*, and most preferably *Bacillus licheniformis. Bacillus subtilis, Bacillus lentus, Bacillus stearothemophilus* or *Bacillus amyloliquefaciens*.

"Homologous protein" or "homologous enzyme" as used herein means two or more proteins or enzymes which are derived from taxonomically identical organisms or which have identical properties. For example two identical cellulases derived from a specific strain of *Bacillus* would be homologous. In contrast, "heterologous proteins" or "heterologous enzymes" as used herein means two or more proteins or enzymes which are derived from taxonomically distinct organisms. For example, a protein derived from distinct genus, such as *E. coli* and *Bacillus licheniformis*, are considered herein to be heterologous. Additionally, a protein derived from taxonomically distinct species, such as *Bacillus amyloliquefaciens* and *Bacillus subtilisin* are considered to be heterologous for the purposes of the present invention. As used herein, two different enzymes derived from the same microorganism, for example the EGI cellulase and the EGII cellulase derived from *T. longibrachiatum*, are considered heterologous.

It is contemplated that a homologous multimer may be useful for such purposes as improving the catalytic activity or efficiency or decreasing the allergenicity when compared to the individual precursor enzyme. For example, in an enzyme dimer produced from two homologous proteases, the resultant protease dimer may exhibit Improved activity or decreased allergenicity over the protease monomer. Alternatively, a multimer may be produced wherein one monomer unit exhibits different enzymatic characteristics from the second monomer unit and yet they work in a complementary manner. For example, in U.S. Pat. No. 4,933,279, the mixture of wild type amylase from *Bacillus licheniformis* and wild type amylase from *Bacillus amyloliquefaciens* is alleged to provide a performance benefit in the liquefaction of starch. As a result, it is contemplated that an enzyme dimer comprising a first monomer unit derived from *Bacillus licheniformis* amylase and a second monomer unit derived from *Bacillus stearothemophilus* would have particular value. Similarly, a first monomer unit derived from a precursor lipase and a second monomer unit derived from a precursor protease would have particular benefits in laundry detergents due to their expected complementary activity on a stain comprising a protein/lipid matrix.

The multimeric enzyme of the present invention differs from naturally occurring enzymes which include two or several subunits. These naturally occurring enzymes are often characterized in that all of the subunits must be present in a specific orientation for enzymatic activity to occur and will contain only one active site in the subunit combination. In fact, the activity of some enzymes is dependent on the enzyme being in multimeric form in that the monomers making up the multimer do not have enzymatic activity of themselves. The specific monomers which make up the multimer are often held together by ionic or hydrophobic interactions, and not by covalent disulfide intermolecular interactions or other chemical linkages mediated through cysteine sulfur reactions as in the present invention. Moreover, the instant invention contemplates the joining of distinct enzymatic units (defined herein as the monomer units) by a disulfide bond(s) thus forming a multimeric enzyme having multiple active sites.

In a preferred embodiment, the enzyme multimer comprises a first monomer unit which has been modified from a corresponding precursor enzyme to include a cysteine residue at an appropriate location. Preferably, the first monomer unit is a derivative of a precursor enzyme and differs due to the site-specific substitution or addition of at least one cysteine residue therein. By "derivative" is meant that the precursor comprises an amino acid sequence which has been modified from its progenitor or parent sequence, through either biochemical, genetic or chemical means, to effect the substitution, deletion or insertion of one or more amino acids. A "derivative" within the scope of this definition should possess desired enzymatic properties observed In the native or parent form to the extent that the derivative is intended to be useful for similar purposes as the precursor. The precursor enzyme may be any enzyme or variant thereof which possesses desired enzymatic activity.

The position within the enzyme at which the added or substituted cysteine residue is located should be selected in such a way to ensure non-interference with the active site reaction mechanism. Thus, in a preferred embodiment, the location of the added or substituted cysteine residue is selected not to be in close proximity with residues which are in the active site or which are critical for substrate binding, more preferably, the added or substituted cysteine are at a relatively large surface displacement from the active site and/or substrate binding site with respect to the total size of the molecule. Thus, in one embodiment, the disulfide bond will involve two cysteine residues which are on or near the surface of the monomer unit at a displacement along the surface of the protein which is maximized with respect to the location of the active site residue or substrate binding residue. Different enzymes will have different tertiary structures which will change the optimal distance for addition or substitution of cysteines so as to limit catalytic or substrate binding interference. However with an enzyme such as protease from *Bacillus lentus* having general dimensions of 45 Å×45 Å×45 Å, it should be possible to place an added or substituted cysteine at a distance of at least 10 Angstroms, preferably 15 Angstroms and most preferably 20 Angstroms. While the existence of a tertiary structure developed through x-ray crystallography will facilitate choosing a location for the added or substituted cysteine, it is possible to obtain such location information without such data. For example, it is possible to map the location of the active site or substrate binding site by cross-linking or other art recognized methods such as tyrosine modification and subsequent activity measurement as in Svendsen, Carlsberg Res. Communication, vol. 41, no. 5, pp. 237–291 (1976) From this data, it will be possible to select known non-active site amino acids which are on the surface of the protein.

Generally, where increased activity is desired, the active sites of the monomer units should be aligned in an appropriate fashion to permit maximum access of the active sites of the monomer units to the substrate. For example, a multimeric protease which is intended to act on a high molecular weight or poorly diffusible substrate, e.g., keratin, would preferably be produced such that the active sites of the monomer units are similarly aligned so as to maximally expose the active sites to the planar substrate. Similarly, it is expected that the activity of a multimeric α-amylase on starch, cellulase on cellulose, or hemicellulase on wood pulp would be enhanced where the active sites are aligned so as to have access to the same substrate surface. Multiple activities may be included within the multimeric enzyme which have synergistic or complementary purposes. For example, a multimeric enzyme comprising a peroxidase and a cellulase for use in detergents would be useful for the dual purposes of treating a cellulosic fabric with the cellulase and preventing dye transfer from dye removed from the cellulose with the bleaching activity of a peroxidase. In this case, it may be advantageous to position the peroxidase active site in such a way that the dye released from the fabric by the cellulase Is bleached by the peroxidase.

By way of specific example, the inventors herein discovered that by altering a serine residue at position +24 in the Bacillus ientus GG36 protease enzyme molecule to cysteine, it was possible to improve the activity profile of the protease. With reference to FIG. 1, it is apparent that the location of the introduced cysteine residues appears to be such that it is on the backside of the molecule with respect to the location of the catalytic site.

The formation of the multimeric enzyme from the individual monomer units can be performed under oxidizing conditions known in the art to facilitate the formation of a thio-mediated bond between two cysteine residues. In general, a disulfide bond will form spontaneously under well known appropriate conditions (e.g., upon contact to oxygen or air) where the substituted or added cysteine on each monomer unit is capable of forming a disulfide bond. Other thio-mediated bonds which are within the invention include the use of linkers produced with N-ethylmaleimide; N,N'-p-phenylenedimaleimide; or bis maleimidohexane.

It Is contemplated that multimeric enzymes according to the present invention will be of use in any application in which enzymes are found to be of use. For example, multimeric enzymes would be useful In any recognized application of enzymes. For example, degrading cellulose or starch to oligosaccharides or glucose, detergents for cleaning, manufacture and laundering of textiles, baking, animal feed additives and manufacture of pulp and paper, are all well known examples of industrially important processes and products to which the application of enzymes has found value and, hence, to which the present invention would provide advantages.

It is an especially surprising result of the present invention that the activity of a specific enzyme or enzymes can be increased by forming a multimeric enzyme comprising the desired activity or activities. As shown in the following examples, it is possible to produce a multimeric enzyme having improved activity in terms of reaction rate compared to an equal concentration of active sites of monomeric enzyme by following the teachings of the invention. Similarly, it is envisioned that the overall activity, the half-life, and performance characteristics such as pH and temperature dependence may be altered in a multimeric enzyme as compared to the monomer unit enzyme, or precursor enzyme, from which it is derived.

The following examples are intended to be illustrative of the invention and should not be interpreted as limiting the scope of the invention.

EXAMPLES

Example 1

Preparation of Protease Dimer GG36

The cloning and the construction for the expression of subtilisin gene (GG36) from *Bacillus lentus* is essentially as described in U.S. Pat. No. 5,185,258, which disclosure is incorporated by reference. The construction of S24C variant of GG36 was performed pursuant to standard oligonucleotide-directed mutagenesis as described in U.S. Pat. No. 5,185,258 and PCT Publication No. WO 95/10615 (Genencor International, Inc.) using the oligonucleotide primer 5' CGTGGATTGAC<u>C</u>GGTT<u>G</u>TGGTGTAAAAGTT 3'
  (SEQ ID NO. 1)

to create the Ser to Cys change at the 24 position of the mature subtilisin sequence. The underlined C residue created the recognition sequence of restriction enzyme AgeI and the underlined G denoted the change from TCT (ser) codon to TGT (cys) codon. Fermentation conditions for preparation of the mutant and wild-type enzymes were as described in U.S. Pat. No. 5,185,258. The GG36-S24C mutant prepared as above was then exposed to air to allow formation of the dimerized mutant.

Example 2

Purification of Protease GG36 Dimer

Ultrafiltrate concentrate of GG36-S24C broth prepared as in Example 1 and treated with DTT was desalted (G25 column) and passed on cation exchange chromatography (BioCad HS/M column) at pH 8.0. Analysis on an SDS-Phast gel system revealed that one fraction contained a dimerized enzyme which had a molecular weight of approximately double that of the wild type monomer GG36 protease Indicating the presence of a dimerized form of GG36-S24C. Subsequent to the cation exchange chromatography, the dimer is sufficiently separated from any non-dimerized protease in the broth to provide only a single band on both native and SDS gels.

Example 3

Comparison of Protease Dimer, Mutant Monomer and Wild Type Enzyme in Skim Milk Hydrolysis Casein Is the major protein in skim milk comprising about 80% of the total protein. The hydrolysis of skim milk is an excellent method of quantifying protease activity due to the presence of many proteins in addition to casein in skim milk The GG36-S24C dimer obtained and purified as in Examples 1 and 2 was tested in a casein hydrolysis assay and compared with GG36 monomer. Wild type GG36 and GG36-S24C were separately prepared to the same concentration (as measured by protease activity) and each solution mixed with 50 mM DTT in 100 mM Tris-HCl (pH 8.6) at 4° C. 10 mM Tris-HCl (pH8.6) with 50 mM DTT without enzyme was used as a control. DTT is used to break any disulfide bonds present in the GG36-S24C dimer.

Skim milk was adjusted to a pH of 10–10.3 with NaOH and 180 μl aliquots were combined with 20 μl of the appropriate enzyme solution (GG36 with or without DTT added and GG36-S24C with or without DTT added) to a resulting concentration of 2, 4 or 8 ppm. A control with and without DTT was also used. The mixtures were then placed in a 96 well microtiter plate and subjected to shaking at 37° C. The turbidity of the solution was measured at 650 nm every 15 minutes for a one hour period in a kinetic microplate reader (Molecular Devices, Inc. Mountain View, Calif.). A decrease in turbidity is indicative of hydrolysis of the protein in the skim milk.

The results are shown in FIGS. 2 and 3. FIG. 2 illustrates that the performance of the S24C monomer was equivalent to the performance of the GG36 monomer. This was necessary because it was not possible to test the S24L monomer against the S24C-dimer under identical conditions, i.e., in either the absence or presence of DTT in both cases. Accordingly, the S24C dimer was compared to GG36 monomer in the absence of DTT, as shown in FIG. 3. The GG36-S24C dimer consistently outperformed the GG36 monomer throughout the course of the experiment it is particularly noteworthy to compare the time needed for the dimer to reach a specific degree of turbidity loss and compare that with the time necessary for the GG36 wild type to reach the same degree of turbidity loss. For example, in FIG. 3 at 15 minutes time, the 2 ppm concentration of GG36-S24C dimer resulted in a turbidity loss of approximately 20%. The time required for the GG36 wild type enzyme to reach a turbidity loss of 20% was approximately double that, e.g., about 30 minutes. This effect is consistently seen in the comparison of the dimer and the wild type monomer on skim milk

Example 4

Comparison of Protease Dimer, Mutant Monomer and Wild Type Enzyme in Keratin Hydrolysis GG36-S24C dimer obtained and purified as in Examples 1 and 2 was tested in a keratin hydrolysis assay and compared with GG36 monomer. Both wild type GG36 and GG36-S24C were prepared to the same concentration and combined with 50 mM DTT in 100 mM Tris-HCl (pH 8.6) at 4° C. 10 mM. Tris-HCl (pH 8.6) with 50 mM DTT without enzyme was used as a control.

Bovine hoof and horn keratin powder (ICN Biomedicals Inc., Cat #90211) was suspended in 100 mM sodium carbonate buffer at pH 10.3 and stirred vigorously for 15 minutes. 1.5 ml of the keratin solution was placed into each well of a 24 well plate and 15 μl of enzyme solution was added at various concentrations (0.8, 0.4, 0.2, 0.1 or 0.0 mg/ml of enzyme) to result in a final concentration of 8, 4, 2 and 0 ppm protein. The mixture was shaken at room temperature and two aliquots of 15 μl were taken from each well at 30 minutes for a two hour period. Each aliquot was placed into 15 μl or reagent A (20:1 0.25M borate and 2.5M NaOH) on a 96 well microtiter plate and mixed with 15 μl of TNBS at a concentration of 3.5 mg/ml. The microtiter plate was shaken at room temperature of 10 minutes and 230 μl of reagent B (105.52 mg $Na_2SO_3$ in 200 ml of 0.212M phosphate pH 4.0) was added. The absorbance at 405 nm was read on a kinetic microplate reader (Molecular Devices, Inc., Mountain View, Calif.) to determine the quantity of free amino groups released by hydrolysis of the keratin in each well.

The results are shown in FIGS. 4 and 5.

---

---

We claim:

1. An enzyme dimer comprising,
   a first *subtilisin* monomer unit having enzymatic activity and a second *subtilisin* monomer unit having enzymatic activity,
   wherein said first *subtilisin* unit and said second *subtilisin* unit are derived from an enzymatically active *Bacillus subtilisin* precursor and said first subtilisin unit and said second *subtilisin* unit differ from the corresponding precursor by the substitution or addition of a cysteine residue therein,
   wherein the cysteine residues are covalently bound to each other through a disulfide bond which attaches the first *subtilisin* unit to the second *subtilisin* unit and wherein the cysteine residues are located at a position other than the catalytically active site and the substrate binding site of each monomer unit, and
   wherein the first monomer unit and the second monomer unit are covalently bound to each other through a disulfide bond located at a position corresponding to residue position 24 of the *Bacillus subtilisin* designated GG36.

2. The enzyme dimer of claim 1, wherein the enzymatically active *Bacillus subtilisin* precursor is selected from the group consisting of *subtilisins* derived from *Bacillus lentus, Bacillus subtilis, Bacillus amyloliquefaciens, Bacillus stearothermophilus* and *Bacillus licheniformis*.

* * * * *